United States Patent [19]
Heinonen

[11] Patent Number: 5,967,141
[45] Date of Patent: *Oct. 19, 1999

[54] METHOD AND APPARATUS FOR METERING AN ANAESTHETIC TO A PATIENT

[75] Inventor: Erkki Heinonen, Helsinki, Finland

[73] Assignee: Instrumentarium Corporation, Helsinki, Finland

[*] Notice: This patent is subject to a terminal disclaimer.

[21] Appl. No.: 08/864,599

[22] Filed: May 28, 1997

Related U.S. Application Data

[63] Continuation of application No. 08/574,787, Dec. 19, 1995, Pat. No. 5,649,531, which is a continuation of application No. 08/331,165, Oct. 28, 1994, abandoned, which is a continuation of application No. 07/975,459, Nov. 12, 1992, abandoned.

[30] Foreign Application Priority Data

Nov. 15, 1991 [FI] Finland ..................................... 915421

[51] Int. Cl.$^6$ .................................................. A61M 15/00
[52] U.S. Cl. ............................... 128/203.12; 128/203.14; 128/203.25
[58] Field of Search ......................... 128/203.12, 203.14, 128/203.25, 204.22

[56] References Cited

U.S. PATENT DOCUMENTS

| | | | |
|---|---|---|---|
| 3,528,418 | 9/1970 | Grosholz et al. | 128/203.14 |
| 4,023,587 | 5/1977 | Dobritz | 128/203.25 |
| 4,191,952 | 3/1980 | Schreiber et al. | 128/203.25 |

(List continued on next page.)

FOREIGN PATENT DOCUMENTS

| | | |
|---|---|---|
| 361134 | 4/1990 | European Pat. Off. . |
| 264554 | 10/1990 | European Pat. Off. . |
| 454390 | 10/1991 | European Pat. Off. . |
| 469797 | 2/1992 | European Pat. Off. . |
| 496336 | 7/1992 | European Pat. Off. . |
| 657183 | 6/1995 | European Pat. Off. . |
| 4105971 | 8/1992 | Germany . |
| 1-280473 | 11/1989 | Japan . |
| 1224478 | 3/1971 | United Kingdom . |
| 2239806 | 7/1991 | United Kingdom . |
| 2239807 | 7/1991 | United Kingdom . |
| 2253149 | 9/1992 | United Kingdom . |

OTHER PUBLICATIONS

Marris et al. "Controlled anaesthesia; a clinical evaluation of an approach using patent characteristics identified during uptake," Brit J. Anaesth 55; 1065–1075 (1983).

Manual "Tec förgasare för kontinverligt flöde" Tec vaporizer for continuous flow), Mediada AB, Nov. 1978.

IEEE Engineering in Medicine & Biology Scoiety 10th Annual International Conference, vol. 10, pp. 578–579.

Primary Examiner—Aaron J. Lewis
Attorney, Agent, or Firm—Andrus, Sceales, Starke & Sawall

[57] ABSTRACT

The invention relates to a method and apparatus for metering to a patient an anaesthetic vaporized from anaesthetic liquid held in a liquid space (27) of a liquid container (18) into a gas space (28). The anaesthetic dose contained in a gas flow supplied to a patient is determined and the dose is adjusted in a manner that the dosage of anaesthetic in a gas intended to be respired by a patient matches a desired dosage and the dosage adjustment of anaesthetic contained in a gas supplied to a patient is effected automatically whenever the current dosage differs from a desired value.

35 Claims, 4 Drawing Sheets

U.S. PATENT DOCUMENTS

| | | | |
|---|---|---|---|
| 4,204,536 | 5/1980 | Albarda | 128/204.22 |
| 4,266,573 | 5/1981 | Braatz | 128/203.25 |
| 4,328,823 | 5/1982 | Schreiber | 128/203.25 |
| 4,442,856 | 4/1984 | Betz | 128/203.14 |
| 4,477,395 | 10/1984 | Albarda | 128/203.14 |
| 4,484,576 | 11/1984 | Albarda | 128/203.27 |
| 4,587,966 | 5/1986 | Albarda | 128/203.27 |
| 4,611,590 | 9/1986 | Ryschka et al. | 128/203.14 |
| 4,770,168 | 9/1988 | Rusz et al. | 128/203.14 |
| 4,798,689 | 1/1989 | Heim et al. | 128/203.25 |
| 4,878,388 | 11/1989 | Loughlin et al. | 128/204.22 |
| 4,881,541 | 11/1989 | Eger, II et al. | 128/203.25 |
| 5,049,317 | 9/1991 | Kiske et al. | 128/203.25 |
| 5,094,235 | 3/1992 | Westenskow et al. | 128/204.22 |
| 5,146,915 | 9/1992 | Montgomery | 128/204.14 |
| 5,161,406 | 11/1992 | Heinonen | 73/23.2 |
| 5,168,866 | 12/1992 | Montgomery | 128/204.14 |
| 5,197,462 | 3/1993 | Falb et al. | 128/203.14 |
| 5,235,971 | 8/1993 | Falb et al. | 128/204.22 |
| 5,243,973 | 9/1993 | Falb et al. | 128/203.25 |
| 5,546,931 | 8/1996 | Rusz | 128/203.12 |
| 5,592,934 | 1/1997 | Thwaites | 128/203.12 |
| 5,649,531 | 7/1997 | Heinonen | 128/203.12 |

METHOD AND APPARATUS FOR METERING AN ANAESTHETIC TO A PATIENT

CROSS-REFERENCE TO RELATED APPLICATIONS

The present application is a continuation application of copending U.S. patent application Ser. No. 08/574,787 filed Dec. 19, 1995, now U.S. Pat. No. 5,649,531, which application is a continuation application of U.S. patent application Ser. No. 08/331,165, filed Oct. 28, 1994, and now abandoned; which application is a continuation application of original U.S. patent application Ser. No. 07/975,459, filed Nov. 12, 1992, and now abandoned.

The present invention relates to an apparatus for metering or dosing an anaesthetic to a patient, said apparatus comprising a liquid container, which encompasses a liquid space containing vaporizable liquid and a gas space, wherein liquid vaporizes, and of a conduit for discharging from the gas space said gas vaporized from the liquid space and of a conduit, which by-passes the gas space for delivering gas to a patient from one or a plurality of containers so as to mix it upstream of a patient with an anaesthetic-containing gas flowing along the conduit. The invention relates also to a method for metering an anaesthetic to a patient.

BACKGROUND OF THE INVENTION

Traditionally in anaesthesia, the respiratory gas administered to a patient is formed in a flow mixer. This is typically linked with a pressurized hospital gas supply system ($O_2$ and $N_2O$), the supply pressures fluctuating within the range of 3–8 bars. The gases are mixed at a desired ratio by regulating the flows by means of adjustable throttle elements and gas-related flowmeters. Downstream of throttle elements and flow measurement the flows are combined. By this time, the pressure has dropped close to ambient external pressure. The compound gas is delivered to an anaesthesia vaporizer for vaporizing anaesthetic vapour therein at a desired concentration. The gas flowing out of the vaporizer is supplied to a patient as alveolar air.

The operation of a conventional anaesthesia vaporizer is based on natural vapour pressure. A fresh gas flow, which thus does not contain the vapour of a vaporizable liquid, is delivered into a liquid container. Here the gas is saturated according to the vapour pressure of a liquid with an anaesthetic vapour. With traditional anaesthetic liquids the boiling point is approximately 50° C. and the vapour pressure at room temperature approximately 25% of the external pressure which is also the concentration of a liquid discharging from the liquid container. Since the desired concentration for a mixture discharging from a vaporizer is about 0.5–5%, the gas flow must be diluted. This is effected by passing just part of the overall flow through a liquid container. By adjusting the ratio of flows passing through and by the container it is possible set the anaesthetic concentration of a gas discharging from the vaporizer as desired. The vaporizers have been calibrated to a diluted anaesthetic concentration.

A new liquid is being introduced in anaesthesia and it termed as 2-(difluoromethoxy)-1,1,1,2-tetrafluoroethane or generally called desphlurane. In terms of its technical qualities relating to vaporization, this differs from traditional liquids in its boiling point, which at normal pressure is 23.5° C. With the boiling point matching the temperature of a normal operating environment, the traditional vaporizing techniques lead to uncontrollable anaesthetic concentration. In the worst case, with the liquid boiling, the anaesthetic vapour discharges into the alveolar air of a patient in a pressurized state, which may quickly result in fatally dangerous concentrations.

In order to control vaporization, an active effort has been made to maintain the liquid temperature above the boiling point. This can be achieved by thermostating the liquid to a desired temperature.

A method based on heating is widely described in U.S. Pat. No. 4,881,541. In this method, the amount of anaesthetic is metered by regulating the flow by means of a needle valve and a rotameter unlike in traditional vaporizers, wherein the regulation was effected by means of concentration. The method has several drawbacks. Since the desphlurane flow is regulated independently of total fresh gas flow, the adjustment error can result in too low a concentration of compound gas $O_2$. In addition, the concentration changes upon adjusting the fresh gas flow. Desphlurane is supplied in glass flasks and the vaporizer is filled just like with conventional inhalation liquids. Prior to filling the container, the liquid supplied in flasks must be cooled to below the boiling point and it must be heated prior to using a vaporizer, which leads to a delay at the start of operation. Therefore, a vaporizer described in the cited Patent includes two parallel vaporizers. The mechanisms designed for traditional vaporizers for securing a minimum oxygen content are not applicable to a described type of vaporizer and, thus, without novel safety mechanisms the apparatus may produce fresh gas mixtures hazardous to a patient.

Separate safety mechanisms are in-built in methods and apparatus described in British Patent application No. 2239807. The apparatus includes an internal pressure regulator for adjusting the anaesthetic vapour supply pressure in patient circulation so as to conform with the prevailing fresh gas flow. By virtue of the apparatus, it is not possible to supply a minor fresh gas flow with a major anaesthetic vapour flow. The prevailing pressure and chemical conditions set a regulator with strict structural requirements: With a minimum fresh gas flow, typically less than 0.5 l/min, the pressure to be regulated is extremely low and, thus, even the mass of a regulator diaphragm may create a problem the same way as the spring forces and kinetic friction of a diaphragm. The chemical environment excludes most rubber types from being used as diaphragm materials. Even the remaining types or qualities have problems relating to deformation and fatigue. On the other hand, in metal diaphragms the spring forces are significant.

The regulator problems are avoided in a method and apparatus described in British Patent application No. 2239806. It describes various methods for preventing the pressure of an anaesthetic vapour produced by boiling liquid from discharging into patient circulation or for preventing the boiling which causes the generation of pressure. In the former case, the pressure of boiling liquid is vented to environment, which is a very poor alternative both in terms of economy, labour hygiene and environment. In the latter case, the liquid temperature is actively maintained below the boiling point by cooling the liquid container by means of a Peltier element. A drawback in activated cooling is a high power demand and a long starting delay, in case the liquid has heated to above the boiling point e.g. during the storage of a vaporizer. Another potential problem is also the dissipation of waste heat generated in cooling. The efficiency of a Peltier element is appr. 30% and, thus, in addition to the amount of heat transferred out of the liquid, there will be a double amount of waste heat produced by the transfer element.

SUMMARY OF THE INVENTION

An object of this invention is to eliminate the above problems. The object is to provide an apparatus and a method for metering an anaesthetic to a patient, said method and apparatus being capable of vaporizing liquids boiling at atmospheric pressure and at a temperature close to that of the operating environment. A particular object is to provide a method and apparatus for metering or dosing an anaesthetic by the name of desphlurane. A further object is to provide a simple and safe apparatus and method for metering an anaesthetic to a patient. Another object is to provide an automatically working solution for metering an anaesthetic. A yet further object is to provide such a method and apparatus for metering an anaesthetic, which is also suitable for application in the metering of traditional anaesthetics. Still another object is to provide such a method and apparatus for metering an anaesthetic, which can be utilized in connection with traditionally designed fresh gas mixing equipment in view of also making use of available mechanisms for securing a minimum oxygen content.

The characterizing features of the invention are set forth in the annexed claims.

In anaesthesia, a patient is supplied with a gas, which is generally a mixture of oxygen and nitrous oxide. This type of gas is generally called fresh gas. Depending on the vaporizing technique of anaesthetic liquid, the fresh gas is either supplied directly to a patient to by-pass a liquid container holding anaesthetic liquid, whereby a gas flow originating from the liquid container merges upstream of the respiratory passages of a patient in this so-called main flow or in a manner that a part of the gas flow, a so-called secondary flow, is passed through a liquid container holding anaesthetic liquid, wherein the gas is admixed with an anaesthetic vapour vaporizing from the liquid container with a result that the flow coming out of the container exceeds that supplied into the container and a part of the gas flow is deflected past the liquid container to be merged later with the flow running through the liquid container.

The invention is based on adjusting a flow discharging from a liquid container including a gas space and a liquid space to match a desired anaesthetic dose to be supplied into a patient circulation as required, whenever the anaesthetic dose tends to diverge too much from a set value. Thus, the object is to measure one way or another the anaesthetic concentration of a gas supplied to a patient during a surgical operation and, should the concentration deviate from desired values, to change the anaesthetic concentration so as to reach a desired concentration. The anaesthetic concentration of a flow emerging from the gas space of a liquid container at below the boiling point tends to alter along with altering conditions. According to the invention, the anaesthetic concentration of a flow delivered to a patient during anaesthesia is monitored and, as the concentration alters, the flow is adjusted in order to maintain the desired concentration within a set range.

Hence, the invention offers a solution which does not necessarily require the heating or cooling of an anaesthetic liquid. Neither is it necessary to effect thermostating to any given temperature. Even during the course of anaesthesia, the anaesthetic liquid container can be maintained at the same temperature as the environment, so time is not wasted for reaching a proper temperature. Even the thermal insulation of a liquid container is not necessary. On the basis of this anaesthetic concentration detected according to the invention, a flow running towards a patient from an anaesthetic liquid container is decreased or increased. Upon vaporization of liquid, the temperature of anaesthetic liquid decreases which in turn leads to a decrease in liquid vaporization. When using a solution of the invention, the variations occurring in degrees of vaporization can be detected and the flow of a gas containing an anaesthetic can be adjusted to match the conditions. Thus, in order to control anaesthetic concentration, the adjustment of a flow originating from the gas space of a liquid container should be effected when necessary if the anaesthetic concentration differs from a desired concentration. The adjustment is preferably effected at certain intervals or periodically. Accordingly, the flow remains unchanged for a certain period of time until, as the anaesthetic concentration alters, the flow is re-adjusted and the gas flow again proceeds according to the latest adjustment up until the moment that the adjustment must be again re-effected etc. In a preferred case, the adjustment is effected at intervals of no more than 30 seconds. More preferably, the adjustment is made at intervals of no more than 20 seconds. The adjustment made at intervals of 5–10 seconds is also good, but most preferably it should be effected at intervals of 10–20 seconds. The anaesthetic concentration or content can be controlled or monitored constantly or, say, as densely as the adjustment of anaesthetic concentration is to be performed.

Determination of the concentration of an anaesthetic supplied to a patient can be effected in several ways. However, a preferred way of doing it is to measure an anaesthetic and fresh gas flow. Prior known are also a variety of analyzers, such as e.g. an infrared analyzer which can also be utilized in the measurement of concentration.

The measurement of anaesthetic flow is preferably effected before the flow emerged from the gas space of a liquid container merges with a fresh gas flow running past it. If the liquid container only discharges anaesthetic vapour, this measurement is sufficient. If, on the other hand, some of the fresh gas is passed through the gas space of a liquid container, the determination of anaesthetic concentration of a gas intended to be respired by a patient requires also that the flow entering a gas space or the temperature of a vaporizable liquid be known. When measuring the incoming flow, the amount of anaesthetic is obtained as a difference between the discharging and incoming flows. The temperature measurement reveals the relative proportion of anaesthetic flow in the flow discharged from a gas space. Presuming that a fresh gas flow is already known, the anaesthetic content to be supplied into a patient circulation is preferably obtained as the proportion of anaesthetic flow from the added total of fresh gas and anaesthetic flows.

An apparatus of the invention comprises a liquid container, from whose liquid space an anaesthetic liquid vaporizes into a gas space and from which an anaesthetic-containing gas is delivered towards a patient through a port or a conduit leading out of the container. Also required is one or a plurality of measuring elements for issuing a signal which is preferably carried to a control element, which interprets the data received thereby into the amount of anaesthetic flowing to a patient and compares the result with a desired amount of vaporized anaesthetic stored in memory. When these differ from each other, the control element performs a correction by means of a regulating element. Upstream of a patient, the vaporized anaesthetic is mixed with another gas respired by a patient, such as a fresh gas.

If desired, the liquid container can be heated whenever necessary for securing the boiling of liquid and the output of vapour even when the passive conduction of heat from the environment is not sufficient. Even in this case, the liquid container does not necessarily require thermostating or heat insulation as the measuring element provides information about the amount of vaporized anaesthetic, whose flow to a patient is regulated. Heating is particularly suitable in a design, wherein the gas space is not supplied with a fresh gas whereby all gas, which discharges from the gas space, consists of vaporized anaesthetic.

An optional solution to heating, a part of the fresh gas flow can be adapted to travel through a gas space included in the liquid container. In view of this, the fresh gas flow conduit is provided with a branch-off point, from which extends on the one hand a flow conduit passing by the liquid container and on the other hand a flow conduit leading into the liquid container's gas space. In this case, the metering of an anaesthetic gas comprises two stages:

At the first stage, as the liquid container temperature exceeds the boiling point of a liquid contained therein, the vapour discharges due to a pressure prevailing in the container into a patient circulation without having to pass some of the fresh gas flow through the liquid container. Regulation of the discharging flow is effected on the basis of the rate of flow measured past the liquid container and the flow, delivered out of the container and consisting by 100% of anaesthetic vapour, in a manner that the anaesthetic concentration of a mixture produced by merging these flows matches a desired value.

At the second stage, when the output of vapour is not sufficient for reaching a desired anaesthetic concentration, a part of the fresh gas flow is carried through a liquid container. The flow of anaesthetic gas discharging from the liquid container is obtained as a difference between flows discharging from and delivered into the liquid container. A regulating element is used to regulate the flow running through the liquid container in a manner that, as the flow running through the liquid container merges with that passing by the liquid container, the resulting mixture has an anaesthetic content or concentration which matches a desired value.

The metering or dosing based on a difference between inlet and outlet flows can be replaced by measuring the temperature of a vaporizable liquid. The anaesthetic concentration of a flow delivered out of the liquid container is determined according to the vapour pressure of a liquid and, thus, if the flow discharging from a liquid container and the temperature of a liquid are known, the anaesthetic vapour flow discharging from a liquid container will be known as well. Particularly, when the temperature is close to the boiling point, the concentration of vapour pressure, and hence also that of the flow delivered out of a liquid container, is sharply a function of temperature provided that a precise measuring of temperature is effected.

BRIEF DESCRIPTION OF THE SEVERAL VIEWS OF THE DRAWING

The invention will now be described in more detail with reference made to the accompanying patent drawings, in which.

DETAILED DESCRIPTION OF THE INVENTION

Figure 1:
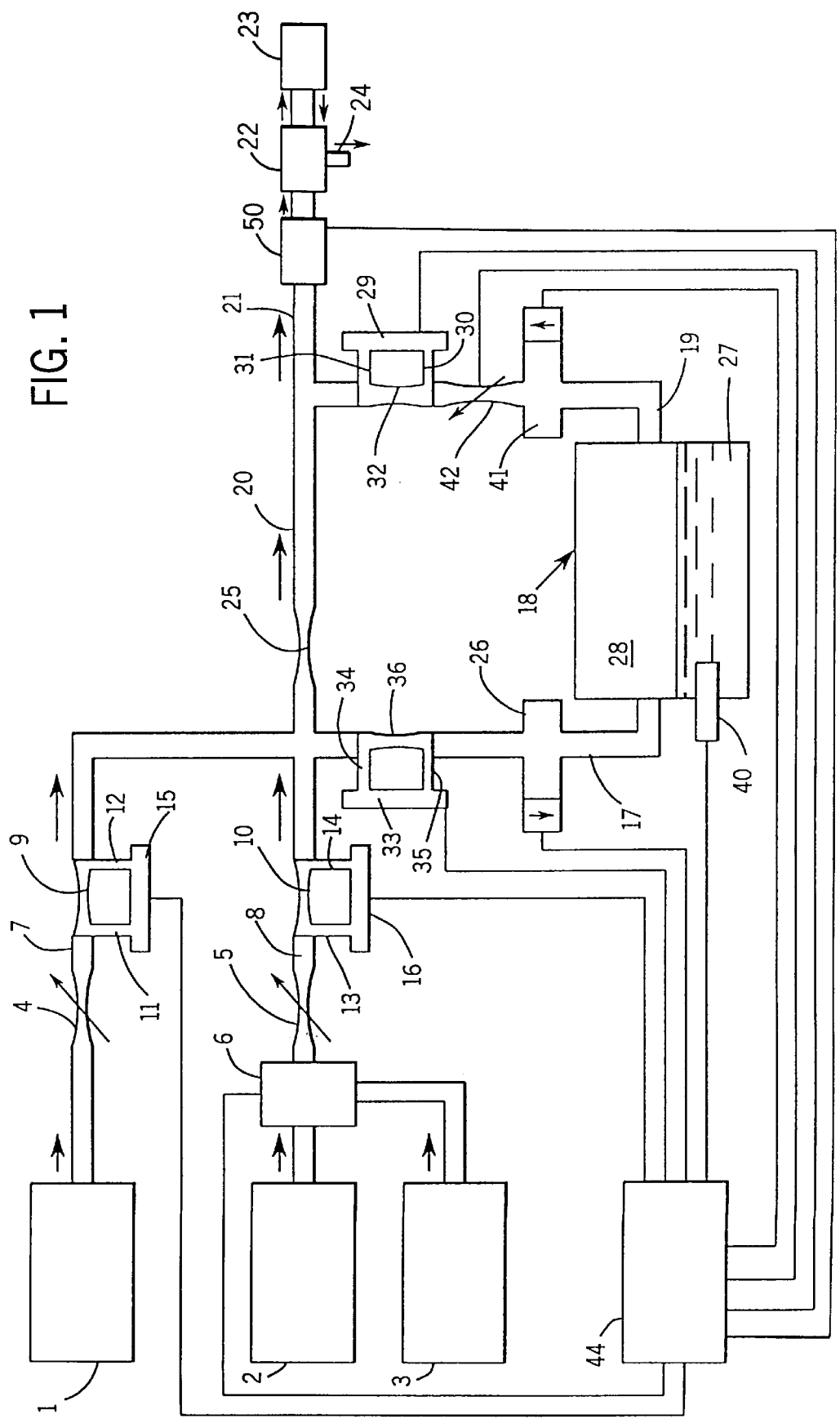
FIG. 1 is a schematic view showing an apparatus of the invention.

FIGS. 1, 2, 3 and 4 primarily illustrate schematic views of solutions applied in the anaesthesia of a patient. These schematic views illustrate, among other things, a few preferred assemblies of the invention, particularly when the employed anaesthetic comprises desphlurane having a boiling point close to room temperature. In these solutions, the elements serving to regulate gas flows from containers 1, 2 and 3 comprise valves 4 and 5, preferably needle valves. The fresh gas comprises for example either a mixture of oxygen and nitrous oxide or optionally that of oxygen and air. Oxygen is contained in a container 1 while a container 2 holds nitrous oxide and a container 3 holds air. A valve 6 is used to select either one of the gases held in containers 2 or 3.

A conduit 7 extending from container 1 and a conduit 8 extending from containers 2 and 3 is each fitted with flow-restricting elements 9 and 10. From both sides of these elements extend measuring conduits 11, 12, 13 and 14 to measuring elements 15 and 16, preferably elements for measuring a pressure difference. The pressure difference can be used in a per se known manner to detect flow rates.

Conduits 7 and 8 extending from the containers join subsequently together and this combined flow of gases is divided in the solutions shown in FIGS. 1, 2 and 3 into two components or into a secondary flow and a primary flow. The secondary flow circulates along a conduit 17 to a liquid container 18 and further along a conduit 19 to merge with the primary flow running along a conduit 20. The combined primary and secondary flow travels along a conduit 21 to a ventilation unit 22 and further to a patient 23. The gas circulated through a patient is delivered back to the ventilation unit, wherefrom it is either recycled in refined state back to a patient or out along a conduit 24.

In the solution shown in FIG. 4, the conduits 7 and 8 extending from containers 1, 2 and 3 also join together subsequently but this combined flow of gases continues along a conduit 20 whereby, unlike in FIGS. 1, 2 and 3, the flow does not travel through liquid container 18 but by-passes it. A conduit 19 extending from the liquid container and a conduit 20 extending from containers 1, 2 and 3 join together and the combined flow continues along a conduit 21 towards a ventilation unit 22 and a patient 23 the same way as in the solutions shown in FIGS. 1, 2 and 3.

Figure 2:
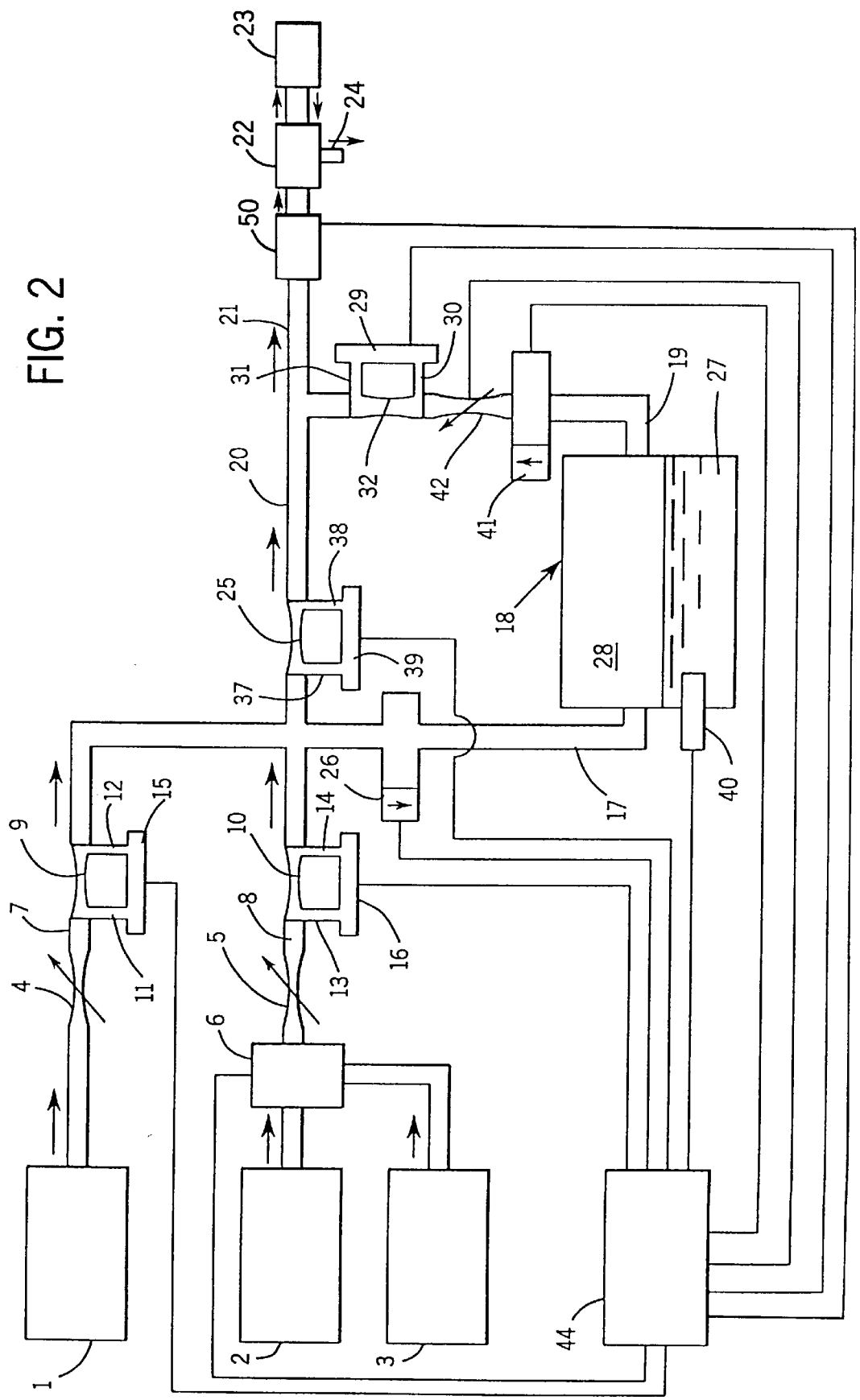
FIG. 2 is a schematic view showing an alternative apparatus of the invention.
Figure 3:
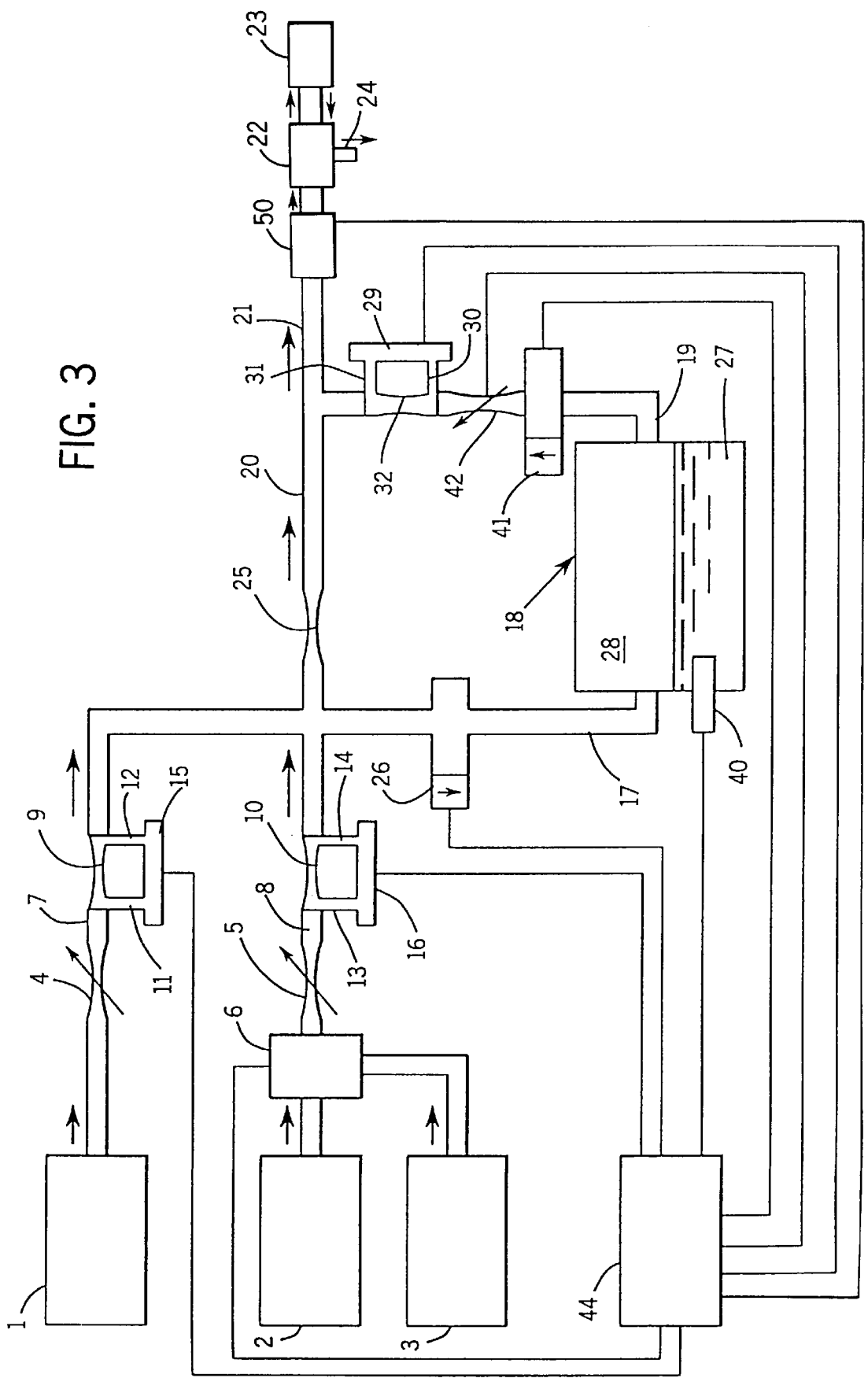
FIG. 3 is a schematic view showing an alternative apparatus of the invention.

The secondary flow is produced in FIGS. 1, 2 and 3 by fitting conduit 20, along which the primary flow progresses, with a flow-restricting element 25. Thus, this element prevents the passage of all flow through conduit 20.

A conduit 17, along which the secondary flow is deflected to liquid container 18, is further fitted with a shut-off element 26 capable of preventing a flow progressing along this conduit. This element is preferably a so-called on-off valve. The valve is only opened whenever the required anaesthetic flow cannot be achieved without a secondary flow, i.e. whenever the output of vapour is not otherwise sufficient.

A liquid container 18 as shown in FIGS. 1–4 includes a liquid space 27 and a gas space 28. An anaesthetic liquid held in the liquid space vaporizes into the gas space, wherefrom the anaesthetic progresses along conduit 19 towards a patient.

There are several alternatives for determining an anaesthetic flow and a fresh gas flow required for the determination of the anaesthetic concentration to be delivered to a patient below the boiling point. FIGS. 1, 2 and 3 illustrate a few preferred solutions. In a highly preferred embodiment, such as the one shown in FIG. 1, a flow originating from a gas space 28 included in a liquid container 18 is measured by means of a measuring element 29, preferably a pressure-difference measuring element. From either side of this measuring element extend measuring ducts 30 and 31 to either side of a flow-restricting element 32 fitted in conduit 19. A flow coming in the liquid container is measured by means of a measuring element 33, which is also preferably a pressure-difference measuring element. From the measuring element extend measuring ducts 34 and 35 to either side of a flow-restricting element 36 fitted in conduit 17. The anaesthetic flow is obtained as a difference between these two flows measured by means of measuring elements 29 and 33. The fresh gas flow is obtained from measuring elements 15 and 16.

In FIG. 2, from either side of a flow-restricting element 25, fitted in a primary-flow carrying conduit 20, extend measuring ducts 37 and 38 to a measuring element 39, which preferably measures a pressure difference that can be used for identifying the flow proceeding along this conduit. When this primary flow is recognized and when the flow proceeding along conduits 7 and 8 extending from the containers is also known, the latter being measured with measuring elements 15 and 16, the secondary flow proceeding along conduit 17 can be found out by deducting the primary flow from the overall fresh gas flow. The anaesthetic flow is obtained by deducting this secondary flow from the flow measured by means of measuring element 29.

In the case of FIG. 3, the fresh gas flow is detected the same way as above. The anaesthetic flow is obtained by measuring a secondary flow downstream of liquid container 18 by means of a measuring element 29, similar to that described above and fitted in conduit 19. The secondary flow contains anaesthetic vaporized from the liquid container, its relative proportion depending on vapour pressure of the liquid. This, in turn, can be determined on the basis of the temperature measuring result. For this purpose the liquid container, which thus includes liquid space 27 and gas space 28, is fitted with a measuring element 40 for measuring temperature of the liquid. In order that the data obtained by means of temperature measurement about vaporization be as close to reality as possible, temperatures close to the boiling point should be avoided.

Also in the solutions shown in FIGS. 1 and 2, temperature of the anaesthetic liquid contained in liquid space 27 of liquid container 18 is monitored by means of a measuring element 40. However, temperature measurement is not absolutely necessary but it offers a safety or back-up system for determining the anaesthetic flow in two different ways, i.e. as described in reference to FIGS. 1 and 2 and also to FIG. 3.

A conduit 19, extending away from liquid container 18 and along which the vaporized anaesthetic is delivered towards a patient, is also preferably fitted with a shut-off element 41 shown in FIGS. 1–4 which can be used for quickly stopping the flow along this conduit whenever necessary, e.g. in an emergency situation. Thus, it can be similar to a shut-off element 26 in conduit 17.

Furthermore, as shown in FIGS. 1–4, said conduit 19 extending away from the liquid container is fitted with a flow regulating element 42, preferably a valve. The regulation is preferably effected by means of a motor control coupled to the valve. This element can be used to regulate the ratio between a primary and a secondary flow and, thus, also the anaesthetic concentration of a gas respired by a patient. The regulation is performed on the basis of a difference between detected anaesthetic flow and desired anaesthetic flow.

When said flow regulating element 42 is electrically controlled, it is possible, depending on the structural design of the element, that during a power failure it will remain in the open position. The boiling of anaesthetic liquid may in this case lead to excessive anaesthetic concentration. This is prevented by means of shut-off element 41 which automatically shuts off said conduit 19 extending out of gas space 28 as electric current is cut off. The shut-off element 26 functions the same way in a conduit leading to the gas space.

Figure 4:
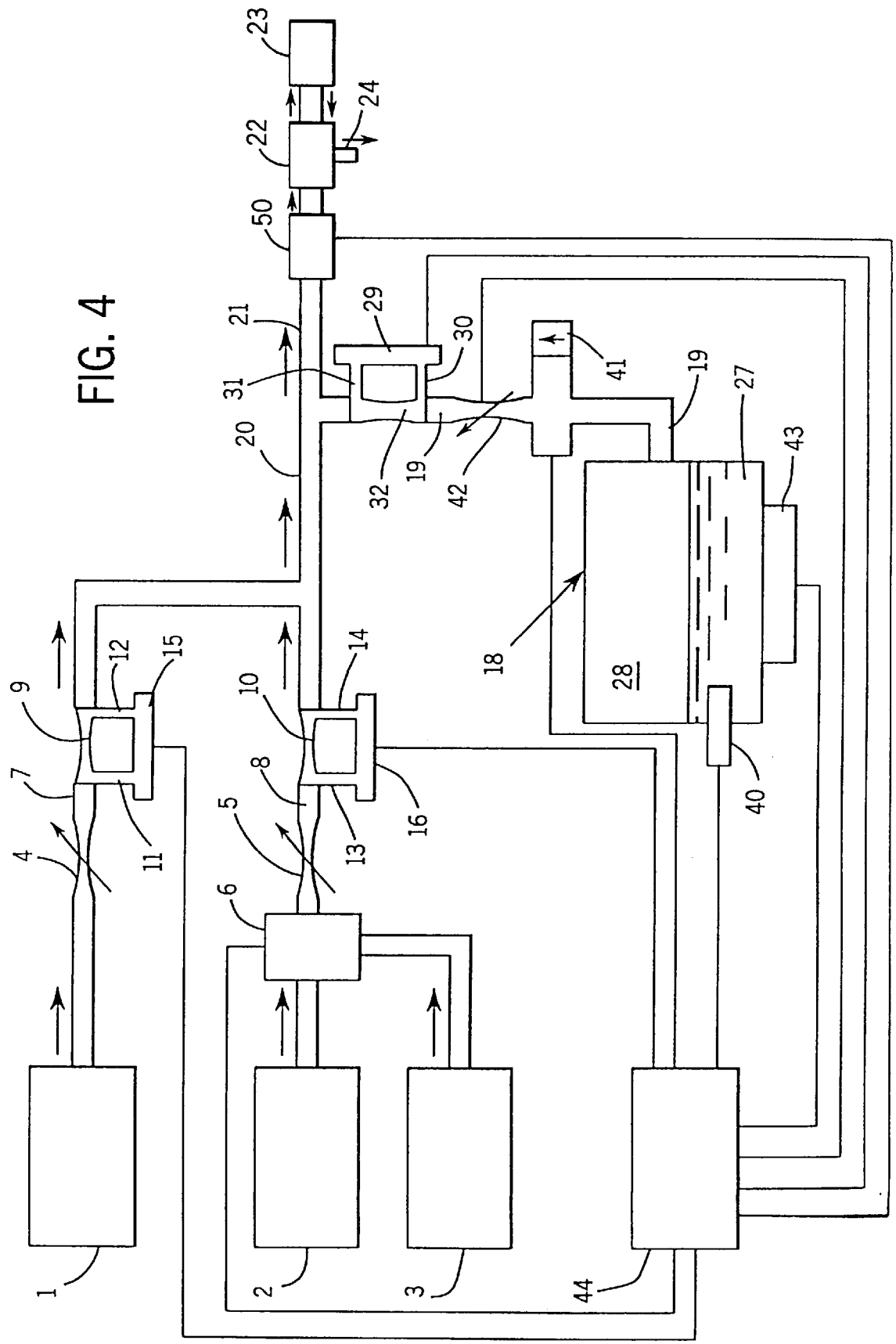
FIG. 4 is a schematic view showing an alternative apparatus of the invention.

Furthermore, FIG. 4 illustrates one possible way of determining the anaesthetic concentration. Hence, in this case there is no secondary flow deflected through gas space 28 of the liquid container. The flow of vapour into said conduit 19 extending therefrom commences upon opening said shut-off element 41. A pressure prevailing in the gas space drives the vapour towards a primary flow running along conduit 20, the vapour being mixed therewith prior to reaching a patient. If the development of vapour in the liquid container becomes weaker, the heating of anaesthetic liquid is commenced. In view of this, the liquid container is fitted with a liquid-temperature regulating element 43, preferably a heating element. In this case, it is preferable that temperature of the liquid contained in liquid space 27 be monitored by means of a measuring element 40. A measuring element 29, which is thus preferably used for measuring a pressure difference prevailing on either side of a flow-restricting element 32 fitted in conduit 19, is capable of determining the amount of anaesthetic flowing in conduit 19. The anaesthetic concentration can be calculated by knowing the pressure differences detected by means of measuring elements 15 and 16 in conduits 7 and 8 extending from gas containers 1, 2 and 3, said pressure differences serving as a basis for finding out the flow. When the combined flow rates of conduits 7 and 8 are known, said flow regulating element 42 fitted in conduit 19 extending away from the liquid container can be used to adjust the flow of anaesthetic proceeding through conduit 19 to be such that the anaesthetic concentration of a gas respired by a patient matches a desired value.

FIGS. 1–4 illustrate measuring elements 15, 16, 29, 33, 39 and 40, from which the measuring data is preferably carried to a control element 44, which is preferably a microprocessor and which is capable of performing mathematical calculations and comparisons of results with previously input values. On the basis of the measuring results, the control element is preferably capable of controlling the action of flow regulating element 42 in order to reach a proper anaesthetic concentration. Also the action of shut-off elements 26 and 41 as well as that of valve 6 and liquid-temperature regulating element 43 are preferably controlled by means of said control element 44.

The control element is capable of monitoring the flow of a vaporized anaesthetic at sufficiently short intervals and, if necessary, of adjusting it by means of said flow regulating element 42. Thus, it would be beneficial to monitor continuously or repeatedly the anaesthetic content or concentration of a gas respired by a patient and, whenever necessary, the thus obtained result can be used to increase or decrease the flow of anaesthetic proceeding along conduit 19. The repeated monitoring or flow regulation is preferably effected at intervals of no more than 30 seconds.

The invention is by no means limited to the above embodiments but various details of the invention can be modified within the scope of the annexed claims. There are other ways of effecting the flow measurement than by measuring just a pressure difference on either side of a flow-restricting element. One alternative solution is based on a generally known mass flow measurement, using a mass-flow measuring element.

Determination of the anaesthetic concentration can also be effected in some other way than by means of a preferred flow measurement or temperature measurement.

One possibility is to employ some sort of spectrometer, such as e.g. a infrared spectrometer.

Neither is determination of the concentration limited to some particular location shown in the drawings but the essential feature in view of the invention is just to find out the anaesthetic concentration of a gas respired by a patient. Thus, the concentration could just as well be measured after the combination of a primary flow and a secondary flow, e.g. from the gas flowing along conduit 21, as by sensor 50.

The number of measuring elements used in determination of the concentration is not significant in view of the invention, either, but the most essential feature is to find out the anaesthetic concentration, which is most preferably effected by measuring a fresh gas flow free of anaesthetic vapour and a 100 percent anaesthetic vapour flow free of fresh gas flow. Instead of two separate measuring elements 15 and 16, the total fresh gas flow can also be measured by a single measuring element from a common conduit. In the case of FIG. 1, the total flow can also be found out e.g. by measuring the primary flow from conduit 20 and the secondary flow from conduit 17.

FIG. 4 illustrates a possibility of heating liquid contained in the liquid container for accelerated vaporization by means of a liquid-temperature regulating element 43. The liquid-temperature regulating element could just as well decrease the liquid temperature, whereby said element would serve as a cooling element. This type of element could be linked e.g. with a liquid container shown in the embodiment of FIG. 1.

The structural solutions described with reference to the drawings can also be utilized in the vaporization of other anaesthetics than just desphlurane.

I claim:

1. Apparatus for metering the amount of anaesthetic supplied to a patient comprising:
    first conduit means (7,8,20,21) having one end for receiving breathable gas from a vessel means and having an other end serving as a gas connection to the patient;
    a container (18) for receiving a vaporizable liquid anaesthetic, said container having a gas space into which the liquid anaesthetic vaporizes;
    second conduit means (19) coupled to said first conduit means at a connection point upstream of the other end of said first conduit means for connecting said gas space of said container to said first conduit means, said second conduit means conducting anaesthetic vapor from said gas space to said first conduit means for mixing with breathable gas for supply to the patient;
    sensor means operatively associated with said first conduit means downstream of said connection point for ascertaining the amount of anaesthetic being supplied to the patient;
    control means (44) coupled to said sensor means for comparing the amount of anaesthetic being supplied to the patient with a desired amount of anaesthetic to be supplied to the patient; and
    a flow constricting valve (42) interposed in said second conduit means and coupled to said control means for altering the amount of anaesthetic vapor flowing in said second conduit means to bring the amount of anaesthetic being supplied to the patient into conformity with a desired concentration of anaesthetic to be supplied to the patient.

2. Apparatus as set forth in claim 1 wherein said sensor means is a spectrometer.

3. Apparatus as set forth in claim 2 wherein said sensor means is an infrared spectrometer.

4. Apparatus as set forth in claim 1 wherein said first conduit means carries only gas from the vessel means upstream of said connection point and said second conduit means carries only anaesthetic vapor.

5. Apparatus as set forth in claim 1 further including third conduit means for connecting said first conduit means to said container at another connection point upstream of said connection point for flowing a portion of the gas from the vessel means through said container.

6. Apparatus as set forth in claim 5 wherein the vessel means includes a plurality of vessels and wherein said first conduit means of said apparatus includes a conduit couplable to each of said vessels, said couplable conduits being joined together upstream of said another connection point.

7. Apparatus as set forth in claim 5 wherein said third conduit means includes further flow sensor means for ascertaining the amount of gas from the vessel means in said third conduit means.

8. Apparatus as set forth in claim 5 wherein said first conduit means includes another flow sensor means, said another flow sensor means ascertaining the amount of gas from the vessel means in said first conduit means upstream of said another connection point and ascertaining the amount of gas from the vessel means in said first conduit means intermediate said connection point and said another connection point.

9. Apparatus as set forth in claim 5 further including a flow restrictor (25) in said first conduit means (20) between said connection point and said another connection point for causing the portion of gas from the vessel means to flow through said container.

10. Apparatus as set forth in claim 5 further including a shut off valve in said third conduit means for controlling gas flow in said third conduit means.

11. Apparatus as set forth in claim 1 wherein said first conduit means includes a flow sensor means for ascertaining the amount of gas from the vessel means in said first conduit means upstream of said connection point.

12. Apparatus as set forth in claim 1 wherein said valve comprises a motor operated valve.

13. Apparatus as set forth in claim 1 wherein said control means comprises a microprocessor.

14. Apparatus as set forth in claim 1 wherein said container includes means for controlling the temperature of the liquid anaesthetic in the container.

15. Apparatus as set forth in claim 1 further defined as apparatus for metering an anaesthetic having a boiling point approximating room temperature.

16. Apparatus as set forth in claim 15 further defined as apparatus for metering desflurane.

17. Apparatus as set forth in claim 1 wherein said second conduit means comprises the sole means of connection between said first conduit means and said container.

18. A method for metering the amount of anaesthetic supplied to a patient, said method comprising the steps of:
    flowing a breathable gas through a first conduit means to the patient;
    vaporizing a liquid anaesthetic in a container to provide an anaesthetic vapor;
    conducting the anaesthetic vapor from the container to said first conduit means via a second conduit means for mixing with the breathable gas flowing through the first conduit means for supply to the patient;
    sensing the amount of anaesthetic conducted within said first conduit means downstream of a point of connection of said first and second conduit means for ascertaining the amount of anaesthetic being supplied to the patient;

establishing a desired concentration of anaesthetic to be supplied to the patient;

comparing the amount of anaesthetic being supplied to the patient with a desired concentration of anaesthetic to be supplied to the patient; and operating a flow constricting valve in said second conduit to alter the amount of anaesthetic vapor conducted in said second conduit means to bring the amount of anaesthetic being supplied to the patient into conformity with the desired concentration of anaesthetic to be supplied to the patient.

19. The method according to claim 18 wherein the step of sensing the amount of anaesthetic is further defined as carrying out the sensing by means of spectroscopy.

20. The method according to claim 18 wherein the step of sensing the amount of anaesthetic is further defined as carrying out the sensing by means of infrared spectroscopy.

21. The method according to claim 18 wherein the step of operating the valve is further defined as periodically operating the valve to alter the amount of anaesthetic vapor.

22. The method according to claim 21 wherein the step of operating the valve is further defined as operating the valve at intervals as frequent as every 30 seconds.

23. The method according to claim 22 wherein the step of operating the valve is further defined as operating the valve at intervals as frequent as every 20 seconds.

24. The method according to claim 21 wherein the step of operating the valve is further defined as operating the valve at intervals of 10–20 seconds.

25. The method according to claim 18 wherein the comparison step is carried out continuously.

26. The method according to claim 18 wherein the comparison step is carried out periodically.

27. The method according to claim 18 further defined as including the steps of:

branching a portion of the gas off the first conduit means through a third conduit means to the container to entrain the anaesthetic vapor;

measuring the amount of gas flow entering the first conduit means;

measuring one of the gas flow in the third conduit means and the gas flow remaining in the first conduit means after branching off the flow through the third conduit means; and measuring the gas flow in second conduit means.

28. The method according to claim 27 defined as including the step of measuring the gas flow in the third conduit means.

29. The method according to claim 27 defined as including the step of measuring the gas flow remaining in the first conduit means after branching off the flow through the third conduit means.

30. The method according to claim 18 further defined as measuring the total amount of gas and anaesthetic vapor supplied to the patient and as determining the ratio of the anaesthetic vapor supplied to the patient to the total amount of gas and anaesthetic vapor supplied to the patient.

31. The method according to claim 18 further defined as including the steps of:

branching a portion of the gas off the first conduit means through a third conduit means to the container to entrain the anaesthetic vapor; and restricting gas flow in the first conduit means downstream of the branching off of the portion of gas to the third conduit means.

32. The method according to claim 18 further defined as a method for metering an anaesthetic having a boiling point approximating room temperature.

33. The method according to claim 32 further defined as a method for metering desflurane.

34. The method according to claim 18 wherein only anaesthesia vapor is conducted from the container to the first conduit means via the second conduit means.

35. The method according to claim 18 further defined as including the steps of:

branching a portion of the gas off the first conduit means through a third conduit means to the container to entrain the anaesthetic vapor; and selectively permitting or preventing gas flow in the third conduit means between the first conduit means and the container.

* * * * *